US008986663B2

(12) United States Patent
Jordan et al.

(10) Patent No.: US 8,986,663 B2
(45) Date of Patent: *Mar. 24, 2015

(54) SKIN CARE COMPOSITIONS

(75) Inventors: Susan L. Jordan, Doylestown, PA (US); Ying O'Connor, Thorndale, PA (US)

(73) Assignees: Rohm and Haas Company, Philadelphia, PA (US); Union Carbide Chemicals & Plastics Technology LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/878,833

(22) PCT Filed: Oct. 27, 2011

(86) PCT No.: PCT/US2011/058053
§ 371 (c)(1),
(2), (4) Date: Apr. 11, 2013

(87) PCT Pub. No.: WO2012/061195
PCT Pub. Date: May 10, 2012

(65) Prior Publication Data
US 2013/0209382 A1    Aug. 15, 2013

Related U.S. Application Data

(60) Provisional application No. 61/410,034, filed on Nov. 4, 2010.

(51) Int. Cl.
*A61K 8/00* (2006.01)
*A61Q 17/04* (2006.01)
*A61K 8/81* (2006.01)
*A61Q 19/08* (2006.01)

(52) U.S. Cl.
CPC ............ *A61K 8/8147* (2013.01); *A61K 8/8111* (2013.01); *A61Q 17/04* (2013.01); *A61Q 19/08* (2013.01); *A61K 2800/34* (2013.01); *A61K 2800/594* (2013.01)
USPC ........................................................ 424/60

(58) Field of Classification Search
USPC ........................................................ 514/23
See application file for complete search history.

(56) References Cited

U.S. PATENT DOCUMENTS

| 4,599,392 | A | 7/1986 | McKinney et al. |
| 4,701,432 | A | 10/1987 | Welborn, Jr. |
| 4,988,781 | A | 1/1991 | McKinney et al. |
| 5,272,236 | A | 12/1993 | Lai et al. |
| 5,322,728 | A | 6/1994 | Davey et al. |
| 5,935,561 | A | 8/1999 | Inman et al. |
| 5,938,437 | A | 8/1999 | Devincenzo |
| 6,180,123 | B1 * | 1/2001 | Mondet .................... 424/401 |
| 6,221,817 | B1 | 4/2001 | Guskey et al. |
| 6,525,157 | B2 | 2/2003 | Cozewith et al. |
| 6,627,184 | B2 | 9/2003 | Coffindaffer et al. |
| 6,696,067 | B2 | 2/2004 | Brandt et al. |
| 6,960,635 | B2 | 11/2005 | Stevens et al. |
| 7,303,744 | B2 | 12/2007 | Wells et al. |
| 7,314,904 | B2 | 1/2008 | Nadolsky et al. |
| 2003/0091512 | A1 | 5/2003 | Adjei et al. |
| 2003/0109391 | A1 | 6/2003 | Midha et al. |
| 2006/0127345 | A1 | 6/2006 | Hilvert et al. |
| 2007/0197729 | A1 | 8/2007 | Wolff et al. |
| 2008/0003195 | A1 | 1/2008 | Arnaud et al. |
| 2008/0020057 | A1 | 1/2008 | Niebauer et al. |
| 2008/0072206 | A1 | 3/2008 | Drasny et al. |
| 2010/0310671 | A1 | 12/2010 | Malotky et al. |
| 2011/0064685 | A1 | 3/2011 | Jordan |
| 2011/0064686 | A1 | 3/2011 | Zhang et al. |
| 2011/0064688 | A1 | 3/2011 | Jordan et al. |

FOREIGN PATENT DOCUMENTS

WO    WO 2009064739 A1 *  5/2009

OTHER PUBLICATIONS

Katagiri, et al., Cover material for foodstuff containing polyethylene, polypropylene, ionomer, ethylene acrylic acid copolymer and/or ethylene methacrylic acid copolymer. 2002. vol. 2003, No. 10. Abstract Only.
Wakabayashi, et al., Micromechanical interpretaion of the modulus of ethylene-(meth_acrylic acid copolymres, 2005, vol. 46, No. 20, pp. 8838-8845.
Wevers, et al., Polyolefin dispersions, an aqueous moisture barrier, 2009.
Clinical Pump & Smooth Lip System Treatment.

* cited by examiner

*Primary Examiner* — Sean Basquill
*Assistant Examiner* — Andrew S Rosenthal
(74) *Attorney, Agent, or Firm* — Edward Brant

(57) ABSTRACT

Described are skin care compositions comprising an aqueous dispersion comprising a metallocene catalyzed polyolefin, an ethylene acrylic acid copolymer, or a combination thereof.

10 Claims, No Drawings

SKIN CARE COMPOSITIONS

CROSS REFERENCE TO RELATED APPLICATIONS

This application is a 35 USC §371 national phase filing of PCT/US2011/058053 filed Oct. 27, 2011, which claims the benefit of U.S. Application No. 61/410,034, filed Nov. 4, 2010.

FIELD

The present application relates to personal care compositions, more specifically, skin care compositions.

BACKGROUND

Skin care compositions are typically designed with a performance benefit in mind, such as imparting humectancy, longer activity through water resistance, visual effects, or other benefits. At the same time, users demand certain aesthetic feel to their skin care compositions. For example, users tend to avoid tacky or sticky compositions, but find smooth and/or soft compositions highly desirable.

Accordingly, what is needed is new skin care compositions that perform well and demonstrate improved aesthetics.

SUMMARY

In one embodiment, the present invention provides skin care compositions, comprising an aqueous dispersion comprising a metallocene catalyzed polyolefin, an ethylene acrylic acid copolymer, or a combination thereof.

DETAILED DESCRIPTION

In one embodiment, the present invention provides skin care compositions, comprising an aqueous dispersion comprising a metallocene catalyzed polyolefin, an ethylene acrylic acid copolymer, or a combination thereof.

In the present invention, "skin care" is intended to refer to personal care compositions for leave on application to the skin, such as lotions, creams, gels, gel creams, serums, toners, wipes, liquid foundations, make-ups, tinted moisturizer, oils, deodorants, and face/ body sprays. "Personal care" relates to compositions to be topically applied to a person (i.e., not ingested). Preferably, the personal care composition is cosmetically acceptable. "Cosmetically acceptable" refers to ingredients typically used in personal care compositions, and is intended to underscore that materials that are toxic when present in the amounts typically found in personal care compositions are not contemplated as part of the present invention.

Metallocene catalyzed polyolefins are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer.

In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™. In one embodiment, the metallocene catalyzed polyolefin is a ethylene/alpha-olefin copolymer, which is commercially available from The Dow Chemical Company, under the tradename INFUSE™.

In one embodiment, the metallocene catalyzed polyolefin comprises at least one of ethylene/octene copolymers, ethylene/butene copolymers, ethylene/hexene copolymers, or ethylene/butene/hexene terpolymers, preferably an ethylene octene copolymer.

In one embodiment, the metallocene catalyzed polyolefin is melt-kneaded in an extruder along with water and a neutralizing agent, such as ammonia, potassium hydroxide, sodium hydroxide, or a combination of the two, to form an aqueous dispersion.

Mechanical dispersion, such as a Parr reactor, is used to create the aqueous dispersion.

In one embodiment, the metallocene catalyzed polyolefin is present in a range from about 10 wt % to about 90 wt % by weight of the aqueous dispersion, preferably in a range from about 15 wt % to about 40 wt %.

The solids content of the aqueous dispersion is in a range from about 10% by weight to about 50% by weight, preferably about 40% by weight.

In turn, the aqueous dispersion is present in a range from about 0.5 wt % to about 10 wt % of solids, preferably about 1 wt % to about 5 wt %, by weight of the personal care composition.

In another embodiment, the aqueous dispersion comprises an ethylene acrylic acid copolymer. Copolymerizing ethylene with acrylic acid yields ethylene-acrylic acid (EAA) copolymers. A preferred ethylene acrylic acid copolymer comprises greater than about 15 wt % acrylic acid, preferably greater than about 17 wt % acrylic acid, more preferably about 20 wt % acrylic acid. It should be understood that ranges recited in this disclosure include all subcombinations of ranges.

A preferred EAA copolymer is PRIMACOR 5990 copolymer (20 wt % acrylic acid), which has a melt index of 1300 g/10 minute (ASTM Method D-1238 at 190° C.) and a Brookfield viscosity of 13,000 cps at 350° F., and is available from The Dow Chemical Company. Another preferred EAA copolymer is PRIMACOR 5980i copolymer (20.5 wt % acrylic acid), which has a melt index of 300 g/10 minute (ASTM Method D-1238 at 190° C.), available from The Dow Chemical Company. EAA copolymers are also available under the tradename NUCREL 2806, available from E.I. du Pont de Nemours and Company, Inc. Ethylene-acrylic acid and ethylene-methacrylic acid copolymers, are described in U.S. Pat. Nos. 4,599,392, 4,988,781, and 5,938,437, each of which is incorporated herein by reference in its entirety.

In yet another embodiment, the aqueous dispersion comprises a metallocene catalyzed polyolefin and an ethylene acrylic acid copolymer.

The ethylene acrylic acid copolymer is present in a range from about 2 wt % to about 35 wt % by weight of the aqueous dispersion, preferably in a range from about 4 wt % to about 20 wt %.

Typically, the ethylene acrylic acid copolymer and metallocene catalyzed polyolefin is in a polymer ratio of about 40:60 to about 15:85.

In some embodiments, the personal care composition includes an emollient. The emollient may be at least one of moisturizer, conditioner, oil, or other fatty substance. For example, when the composition is in an emulsion form, it comprises at least one oily phase that contains at least one oil, especially a cosmetically acceptable oil. The term "oil" means a fatty substance that is liquid at room temperature.

Examples of oils include hydrocarbon-based oils of animal origin, such as squalene, hydrocarbon-based oils of plant origin, such as liquid triglycerides of fatty acids comprising from 4 to 10 carbon atoms, for instance heptanoic or octanoic acid triglycerides, or alternatively, oils of plant origin, for example sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, or caprylic/capric acid triglycerides, MIGLYOL 810, 812 and 818 (from Dynamit Nobel), synthetic esters and ethers, especially of fatty acids, for instance the oils of formulae $R^1COOR^2$ and $R^1OR^2$ in which $R^1$ represents a fatty acid residue comprising from 8 to 29 carbon atoms and $R^2$ represents a branched or unbranched hydrocarbon-based chain comprising from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate, hydroxylated esters, for instance isostearyl lactate, octyl hydroxystearate, octyldodecyl hydroxystearate, diisostearyl malate, triisocetyl citrate and fatty alcohol heptanoates, octanoates and decanoates, polyol esters, for instance propylene glycol dioctanoate, neopentyl glycol diheptanoate and diethylene glycol diisononanoate, pentaerythritol esters, for instance pentaerythrityl tetraisostearate, lipophilic derivatives of amino acids, such as isopropyl lauroyl sarcosinate, such as is sold under the name ELDEW SL 205 (from Ajinomoto), linear or branched hydrocarbons of mineral or synthetic origin, such as mineral oils (mixtures of petroleum-derived hydrocarbon-based oils), volatile or non-volatile liquid paraffins, and derivatives thereof, petroleum jelly, polydecenes, isohexadecane, isododecane, hydrogenated isoparaffin (or polyisobutene), silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, ethers such as dicaprylyl ether (CTFA name: dicaprylyl ether), and $C_{12}$-$C_{15}$ fatty alcohol benzoates (FINSOLV TN from Finetex), mixtures thereof.

Oils include mineral oil, lanolin oil, coconut oil and derivatives thereof, cocoa butter, olive oil, almond oil, macadamia nut oil, aloe extracts such as aloe vera lipoquinone, jojoba oils, safflower oil, corn oil, liquid lanolin, cottonseed oil, peanut oil, hydrogenated vegetable oil, squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, and the oil of cereal germs.

Other suitable emollients include dicaprylyl ether, $C_{12-15}$ alkyl benzoate, DC 200 FLUID 350 silicone fluid (from Dow Corning Corp.), isopropyl palmitate, octyl palmitate, isopropyl myristate, hexadecyl stearate, butyl stearate, decyl oleate, acetyl glycerides, the octanoates and benzoates of $C_{12-15}$ alcohols, the octanoates and decanoates of alcohols and polyalcohols such as those of glycol and glyceryl, ricinoleates esters such as isopropyl adipate, hexyl laurate and octyl dodecanoate, dicaprylyl maleate, phenyltrimethicone, and aloe vera extract. Solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate.

In one embodiment, the emollient is present in an amount from about 0.05% to about 40% by weight of the composition. Preferably, the emollient is present in an amount from about 0.1% to about 10% by weight of the composition.

In some embodiments, the personal care composition includes an emulsifier or a surfactant. Suitable emulsifiers are selected from amphoteric, anionic, cationic and nonionic emulsifiers, used alone or as a mixture. Anionic surfactants include soaps or salts of fatty acids, alkyl sulfates, alkyl ether sulfates, alpha-olefin sulfonates, alkyl aryl sulfonates, sarcosinates, alkyl glucose esters or their alkoxylates, and in particular sodium lauryl sulfate, ammonium lauryl sulfate, triethanolamine lauryl sulfate, sodium laureth sulfate, isethionates, and triethanolamine stearate. Nonionic surfactants include methyl glucose stearates or their ethoxylates, alkyl polyglucosides, and glycerol monostearate, fatty acid alkanol amides, alkyl aryl polyglycol ether, polyglycol ethers and in particular cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl .beta.-aminopropionates, betaines, alkyl imidazolines and in particular cocamidopropyl betaine and caproam phocarboxy propionate. Polymeric cationic emulsifiers that include hydrophobic moieties are preferred, examples of which include polyquaternium-24 and polyquatemium 67 (SOFTCAT™), available from The Dow Chemical Company.

Emulsions free of emulsifying surfactants or comprising less than 0.5% of emulsifying surfactants relative to the total weight of the composition may also be prepared, by using suitable compounds, for example polymers having emulsifying properties, such as CARBOPOL 1342 polymer (Noveon), PEMULEN polymer (Noveon), SEPIGEL 305 polyacrylamide/C13-C14 isoparaffin/laureth-7 (Seppic), particles of ionic or nonionic polymers, particles of anionic polymer such as, isophthalic acid, sulfoisophthalic acid polymers, and phthalate/sulfoisophthalate/glycol copolymers (for example diethylene glycol/phthalate/isophthalate/1,4-cyclohexanedimethanol sold under the names Eastman AQ diglycol/ CHDM/isophthalates/SIP copolymer (AQ35S, AQ38S, AQ55S and/or AQ48 Ultra, from Eastman Chemical). Emulsifier-free emulsions stabilized with silicone particles or metal oxide particles such as $TiO_2$ or the like may also be prepared.

The emulsifier or surfactant may be present in an amount from about 0.01% to about 15% by weight of the composition. In one embodiment, the surfactant is present in an amount from about 0.1% to about 5% by weight of the composition.

In some embodiments, the personal care composition includes a thickener. Examples of thickeners include polymers, for example, modified or unmodified carboxyvinyl polymers, such as the products sold under the names CARBOPOL and PEMULEN (INCI name: Acrylates/C10-30 alkyl acrylate crosspolymer; available from Noveon), polyacrylates and polymethacrylates, such as the products sold under the names LUBRAJEL and NORGEL (from Guardian) or HISPAGEL (from Hispano Chimica), polyacrylamides, 2-acrylamido-2-methylpropanesulfonic acid polymers and copolymers, which are optionally crosslinked and/or neutralized, for instance the poly(2-acrylamido-2-methylpropanesulfonic acid) sold by Clariant (INCI name: ammonium polyacryldimethyltauramide), emulsified crosslinked anionic copolymers of acrylamide and AMPS, such as those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate copolymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulose and hydroxypropylcellulose, associative polymers, for instance associative polyurethanes, copolymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (from Hüls America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (from Rohm & Haas). One preferred thickener is METHOCEL hydroxypropyl methylcellulose, available from The Dow Chemical Company.

In one embodiment, the thickener is present in an amount from about 0.01% to about 10% by weight of the composition. In one embodiment, the thickener is present in an amount from about 0.1% to about 5% by weight of the composition.

The personal care composition also comprises a suitable carrier, or mixtures of carriers. The type of carrier depends on the particular end use of the composition. Illustrative carriers include, for example, water, such as deionized or distilled water, emulsions, such as oil-in-water or water-in-oil emulsions, alcohols, such as ethanol, isopropanol or the like, glycols, such as propylene glycol, glycerine or the like, or combinations thereof. A preferred carrier is deionized water.

In one embodiment, the personal care compositions of the present invention further comprise an active ingredient selected from skin care actives, nail care actives, or hair care actives. Actives include sunscreens, skin colorants, drug substances (such as anti-inflammatory agents, antibiotics, topical anesthetics, antimycotics, keratolytics, and the like), skin protectants, conditioners, humectants, and ultraviolet radiation absorbers.

Examples of sunscreens include para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PABA, glyceryl aminobenzoate, and lawsone with dihydroxy acetone and red petrolatum.

In one embodiment, the personal care compositions of the present invention further comprise at least one additional ingredient. Optional ingredients include any suitable substance for personal care compositions, for example, colorants, preservatives, pH adjustors, reducing agents, fragrances, foaming agents, tanning agents, depilatory agents, astringents, antiseptics, deodorants, antiperspirants, insect repellants, and biocides.

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes may also optionally be used.

Preservatives include alcohols, aldehydes, methylchloroisothiazolinone and methylisothiazolinone, p-hydroxybenzoates, and in particular methylparaben, propylparaben, glutaraldehyde and ethyl alcohol.

The pH adjustors, include inorganic and organic acids and bases and in particular aqueous ammonia, citric acid, phosphoric acid, acetic acid, sodium hydroxide, potassium hydroxide, and triethanolamine. In a preferred embodiment, the pH adjustor is aminomethyl propanol, L-arginine, tromethamine, PEG-15 cocamine, diisopropanolamine, triisopropanolamine, or tetrahydroxypropyl ethylenediamine In a particularly preferred embodiment, the pH adjustor is amino methyl propanol, Aminomethyl propanol is available under the tradename AMP-ULTRA from Angus Chemical Company. In one embodiment, the pH adjustor is present in an amount from about 0.01% to about 1% by weight of the composition. In one embodiment, the pH adjustor is present in an amount from about 0.1% to about 0.5% by weight of the composition.

Reducing agents include ammonium thioglycolate, hydroquinone and sodium thioglycolate.

Fragrances include any component which provides a pleasant scent. Fragrances are generally aldehydes or ketones, and often oils obtained by extraction of natural substances or synthetically produced. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

The amount of optional ingredients effective for achieving the desired property provided by such ingredients can be readily determined by one skilled in the art. In use, the skin care compositions are applied in a conventional manner.

EXAMPLES

The following examples are for illustrative purposes only and are not intended to limit the scope of the present invention. All percentages are by weight unless otherwise specified.

Example 1

Personal care compositions of the present invention include aqueous dispersions comprising metallocene catalyzed polyolefin, preferably in the presence of an ethylene acrylic acid copolymer. Examples of such aqueous dispersions include the following:

Batch 1

A 42% solids aqueous dispersion of ethylene acrylic acid and metallocene catalyzed polyolefin, commercially available from The Dow Chemical Company under the tradename DPOD 4501, produced using Dow's BLUEWAVE technology.

Batch 2

A 52% solids aqueous dispersion of ethylene acrylic acid and metallocene catalyzed polyolefin, commercially available from The Dow Chemical Company under the tradename DPOD 4503, produced using Dow's BLUEWAVE technology.

Batch 3

A pH ~11 aqueous dispersion of ethylene/1-octene copolymer with potassium behenoate. Feed 10,000 parts ethylene/1-octene copolymer (ENGAGE® 8200) into a resin hopper of a polymer extruder together with 300 parts (active weight) of dispersant (Behenic acid, a dispersant containing a 22 carbon chain fatty acid as active component), and melt-knead by a single extruder at about 160° C. to give a molten polymer/behenic acid blend (molten blend). Thereafter, into the barrel of a twin-screw extrude, pump a solution of 32 parts potassium hydroxide (KOH) dissolved in 398 parts deionized water into the molten blend under pressure and at a temperature of about 165° C. As the molten blend/aqueous KOH mixture passes down the barrel of the extruder, add deionized water until producing a dispersion having about 40 wt % to 60 wt % solids. Cool the dispersion to below 90° C. before extruding and collecting.

Batch 4

An aqueous dispersion comprising an ethylene acrylic acid copolymer is prepared as follows. PRIMACOR 5980i 20% ethylene acrylic acid resin (60 g), potassium hydroxide (25 g of 30 wt. %), and water (21 g) are placed in a 300 mL Parr reactor vessel fitted with a Cowles blade. The material is heated to 120° C. while mixing slowly. Once the set temperature is reached, the mixer is run on high (~1800 rpm) for 25 minutes. While still mixing on high, the sample is diluted with water fed into the reactor with an HPLC pump at a rate of 40 mL/min to the desired concentration of 25.7% solids by weight based on the amount of ethylene acrylic acid resin. Heat is removed and stirring continues until the temperature cools to at least 45° C. The Parr is then opened and the dispersion is collected.

Example 2

Exemplary sunscreen lotions of the present invention contain the components recited in TABLE 1 on a weight/weight basis (wt. %).

TABLE 1

|   |   | Batch A | Batch B |
|---|---|---|---|
| A | Propylene glycol | 3 | 3 |
|   | NIPAGUARD Propylene Glycol, Diazolidinyl Urea, Methyl Paraben, Propyl Paraben preservative (available from Clariant) | 1 | 1 |
|   | Water | 61.5 | 61.5 |
| B | EMULGADE 1000 Cetearyl Alcohol and Ceteareth 20 | 3 | 3 |
|   | Cetearyl Alcohol | 1 | 1 |
|   | DERMOL OMC octyl methoxycinnamate | 7.5 | 7.5 |
|   | UVINOL M40 benzophenone-3 | 3 | 3 |
|   | DERMOL BLOCK 2-ethylhexyl salicylate | 5 | 5 |
|   | CETIAL AB $C_{12-15}$ alkyl benzoate | 8 | 8 |
| C | Batch 1 Ethylene/octane copolymer and ethylene/sodium acrylate copolymer (42%) | 7 | — |
|   | Batch 2 Ethylene/octane copolymer and ethylene/sodium acrylate copolymer (52%) | — | 7 |

The oil phase ingredients (B) are placed in a small container in an 80° C. oven for the solids to melt and a solution to form. The water phase ingredients (A) are mixed and heated to about 80° C. while stiffing. The water and oil phases are then combined at about 80° C. and mixed until uniform. If necessary, the resulting solution may be homogenized at about 11,000 rpm until the formulation is emulsified. The formulation is then cooled to room temperature, and the appropriate polymer ingredient (C) is added.

Example 3 (Comparative)

Comparative sunscreen lotions contain the components recited in TABLE 2 on a weight/weight basis (wt. %). ht basis (wt. %).

TABLE 2

|   |   | Comparative Batch Z |
|---|---|---|
| A | GANEX 216 PVP/hexadecene copolymer | 3.5 |
|   | Propylene glycol | 3 |
|   | NIPAGUARD Propylene Glycol, Diazolidinyl Urea, Methyl Paraben, Propyl Paraben preservative | 1 |
|   | Water | 62 |
| B | EMULGADE 1000 Cetearyl Alcohol and Ceteareth 20 | 3 |
|   | Cetearyl Alcohol | 1 |
|   | DERMOL OMC octyl methoxycinnamate | 7.5 |
|   | UVINOL M40 benzophenone-3 | 3 |
|   | DERMOL BLOCK 2-ethylhexyl salicylate | 5 |
|   | CETIAL AB C12-15 alkyl benzoate | 8 |

Comparative Batch Z contains a commercial film former (PVP/hexadecene copolymer), but is prepared substantially according to the protocol of Example 2.

Example 4

Compositions substantially according to the protocols of Examples 2 and 3 were prepared. In the water resistance test, 0.05 ml of the sunscreen lotion is applied to a simulated rough skin surface of a pre-hydrated VITRO-SKIN substrate (available from IMS Inc.) with a syringe. The sample then is distributed evenly over the entire surface area by using a gloved finger and allowed to dry for 30 minutes.

The dried sample is then soaked with 35 grams of deionized water in a 80 ml vial and shaken for 20 minutes at maximum agitation with a shaker. The remaining sunscreen agent on the skin is extracted with 50% isopropyl alcohol solution. Similarly, the sun screen agent in the wash water is extracted (with 50% isopropyl alcohol solution). The amount of sunscreen agent in the extracted solutions is measured by a UV spectrophotometer.

The sunscreen lotions according to the present invention were tested against the comparative sample of Example 3 for water resistance using a water resistance testing protocol substantially similar to that described above.

Batch A, a sunscreen lotion according to the present invention, lost only 11.66% of the sunscreen active in the rinse. Batch B, a sunscreen lotion according to the present invention, lost only 4.16% of the sunscreen active in the rinse. By comparison, Comparative Batch Z lost 18.65%. Accordingly, the sunscreen lotions according to the present invention provide greatly improved waterproofing over the known composition.

Example 5

Exemplary skin lotions of the present invention contain the components recited in TABLE 3 on a weight/weight basis (wt. %).

TABLE 3

| Part | | Batch C |
|---|---|---|
| A | Water | Q.S. to 100 |
| | Glycerin | 2 |
| | KELTROL CG-SFT Xanthan Gum | 0.7 |
| B | PROCOL CS-20-D Cetearyl Alcohol and Ceteareth 20 | 3 |
| | THOROCOEST CMS Glyceryl Stearate | 2 |
| | CARNATION WHITE Mineral Oil | 5 |
| | SUPER WHITE PROTOPET Petrolatum | 10 |
| | Batch 1 Ethylene/octane copolymer and ethylene/sodium acrylate copolymer (42%) | 11.9 |
| C | GLYDANT DMDM Hydantoin Citric Acid (50%) | 0.3 dropwise to pH 5.5~6.5 |

Glycerin is combined with Xanthan Gum, and then this mixture is added to water (A). Heat part A to 75-80° C. while mixing. Add the first four ingredients of part B in a seperate vessel, heat it to 75-80° C., then add it to part A slowly with high speed mixing. Stir for a few minutes at 75-80° C., then add Ethylene/octane copolymer and ethylene/sodium acrylate copolymer to combined parts A&B while mixing. Adjust pH below 7 with Citric Acid and begin cooling. Add remaining part C at 45-50° C., slowly cool to 30° C.

In the present embodiment, the Xanthan Gum acts as the thickener and the suspending agent, CETEARETH 20 is the primary emulsifier, and Cetearyl Alcohol and Glyceryl Stearate are the co-emulsifiers, with petrolatum and mineral oil as the emollients.

Example 6 (Comparative)

Comparative skin lotions of the present invention contain the components recited in TABLE 4 on a weight/weight basis (wt. %).

TABLE 4

| Part | | Comparative Batch X | Comparative Batch Y |
|---|---|---|---|
| A | Water | Q.S. to 100 | Q.S. to 100 |
| | Glycerin | 2 | 2 |
| | KELTROL CG-SFT Xanthan Gum | 0.7 | 0.7 |
| B | PROCOL CS-20-D Cetearyl Alcohol and Ceteareth 20 | 3 | 3 |
| | THOROCOEST CMS Glyceryl Stearate | 2 | 2 |
| | CARNATION WHITE Mineral Oil | 5 | 5 |
| | SUPER WHITE PROTOPET Petrolatum | 10 | 10 |
| | DOW CORNING 9701 Powder (100% solids) Dimethicone/Vinyl Dimethicone Crosspolymer (and) Silica | 5 | — |
| C | GLYDANT DMDM Hydantoin Citric Acid (50%) | 0.3 dropwise to pH 5.5~6.5 | 0.3 dropwise to pH 5.5~6.5 |

Comparative Batch X contains a commercial sensory modifier (silicone; silky-powdery skin feel; wrinkle masking), but is prepared substantially according to the protocol of Example 5.

Example 7

Compositions substantially according to the protocols of Examples 5 and 6 were prepared. In the sensory test, 2 mg/cm$^2$ of a composition is dispensed on the inside of the one forearm of a trained panelist, and 2 mg/cm$^2$ of a comparative composition is dispensed on the other forearm. The following parameters are evaluated, rated from -3 (significantly worse than control) to +3 (significantly better than control), by the trained panelist. The parameters are Ease of Spreading, Absorption, Tackiness, Oiliness, Waxiness, Smoothness (initial, 30 minutes, and 60 minutes, after application), Softness (initial and 30 minutes after application), and Matte Finish (lack of Shine).

In such a comparison, a trained panelist compared inventive Batch C to Comparative Batch Y, and found that Batch C was slightly better in every category except initial smoothness, where Batch C was +2, and ease of spread, where they were the same. This overall better sensory performance indicates that the inventive compositions can be used as a sensory modifier to improve the aesthetic feel for leave-on skin care applications.

In another such comparison, a trained panelist compared inventive Batch C to Comparative Batch X, which contained a commercial sensory modifier, and found that Batch C was slightly better in 30 minute smoothness and 30 minute softness, and the same in all other categories except slightly worse (-1) in spreading, absorption, tackiness, oiliness, and waxiness. This basically equivalent sensory performance is very encouraging, as silicone sensory modifiers are relatively expensive, effectively limiting their use to higher end products, which limits accessibility by consumers. Accordingly, in one embodiment, the inventive compositions can be used as partial or complete silicone sensory modifier replacements.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this specification are hereby incorporated by reference herein, in their entireties.

The invention claimed is:

1. A water resistant skin care composition, comprising:
    an aqueous dispersion comprising a metallocene catalyzed polyolefin and an ethylene acrylic acid copolymer;
    propylene glycol; and
    a sunscreen comprising para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, or salicylates.

2. The skin care composition of claim 1, wherein the ethylene acrylic acid copolymer is present in a range from 4 wt % to 20 wt % by weight of the aqueous dispersion.

3. The skin care composition of claim 1, wherein the metallocene catalyzed polyolefin is present in a range from 15 wt % to 40 wt % by weight of the aqueous dispersion.

4. The skin care composition of claim 1, wherein the aqueous dispersion is present in a range from 0.5 wt % to 20 wt % by weight of the skin care composition.

5. The skin care composition of claim 1, wherein the sunscreen comprises octyl methoxycinnamate.

6. The skin care composition of claim 1, wherein the sunscreen comprises avobenzone.

7. The skin care composition of claim 1, wherein the metallocene catalyzed polyolefin comprises an ethylene/octene copolymer.

8. The skin care composition of claim 1, wherein the ethylene acrylic acid copolymer is present in a range of from 2 wt % to 35 wt %.

9. The skin care composition of claim 1, wherein the metallocene catalyzed polyolefin is present in a range of from 10 wt % to 90 wt % by weight of the aqueous dispersion.

10. The skin care composition of claim 1, wherein the aqueous dispersion is present in a range of from 1 wt % to 5 wt % by weight of the skin care composition.

* * * * *